(12) United States Patent
Nolan et al.

(10) Patent No.: US 10,799,261 B2
(45) Date of Patent: Oct. 13, 2020

(54) RETAINING POLYPECTOMY DEVICE

(71) Applicant: Boston Scientific Scimed, Inc., Maple Grove, MN (US)

(72) Inventors: Damien Vincent Nolan, Galway (IE); Martyn G. Folan, Galway (IE); Matthew Montague, Galway (IE); Martin Hynes, Galway (IE); Enda Connaughton, Galway (IE); Thomas Keating, Galway (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 207 days.

(21) Appl. No.: 15/679,556

(22) Filed: Aug. 17, 2017

(65) Prior Publication Data

US 2018/0049766 A1    Feb. 22, 2018

Related U.S. Application Data

(60) Provisional application No. 62/376,492, filed on Aug. 18, 2016.

(51) Int. Cl.
*A61B 17/3205* (2006.01)
*A61B 17/32* (2006.01)
*A61B 17/221* (2006.01)
*A61B 17/00* (2006.01)

(52) U.S. Cl.
CPC ...... *A61B 17/32056* (2013.01); *A61B 17/221* (2013.01); *A61B 17/320016* (2013.01); *A61B 2017/0046* (2013.01); *A61B 2017/00269* (2013.01); *A61B 2017/00353* (2013.01)

(58) Field of Classification Search
CPC ...... A61B 17/32056; A61B 2017/2217; A61B 2017/2212; A61B 17/221
See application file for complete search history.

(56) References Cited

U.S. PATENT DOCUMENTS

| 3,791,387 | A | * | 2/1974 | Itoh | A61B 17/29 606/113 |
| 5,336,227 | A | * | 8/1994 | Nakao | A61B 17/32056 600/106 |
| 6,015,415 | A | | 1/2000 | Avellanet | |
| 6,224,612 | B1 | * | 5/2001 | Bates | A61B 17/221 606/114 |
| 6,264,663 | B1 | * | 7/2001 | Cano | A01N 59/00 606/110 |
| 6,814,739 | B2 | | 11/2004 | Secrest et al. | |
| 7,618,437 | B2 | | 11/2009 | Nakao | |
| 8,206,401 | B2 | | 6/2012 | Nakao | |
| 8,435,237 | B2 | | 5/2013 | Bahney | |
| 8,932,211 | B2 | | 1/2015 | Piskun et al. | |

* cited by examiner

*Primary Examiner* — Shaun L David
*Assistant Examiner* — Christina C Lauer
(74) *Attorney, Agent, or Firm* — Bookoff McAndrews, PLLC

(57) ABSTRACT

A medical device may include a snare loop and an elastic member that connects at least two sides of the snare loop. The elastic member is configured to transition from an unexpanded state where the elastic member is in a plane of the snare loop to an expanded state where the elastic member is outside the plane of the snare loop. The snare loop has a same shape when the elastic member is in the unexpanded shape and the expanded shape.

20 Claims, 3 Drawing Sheets

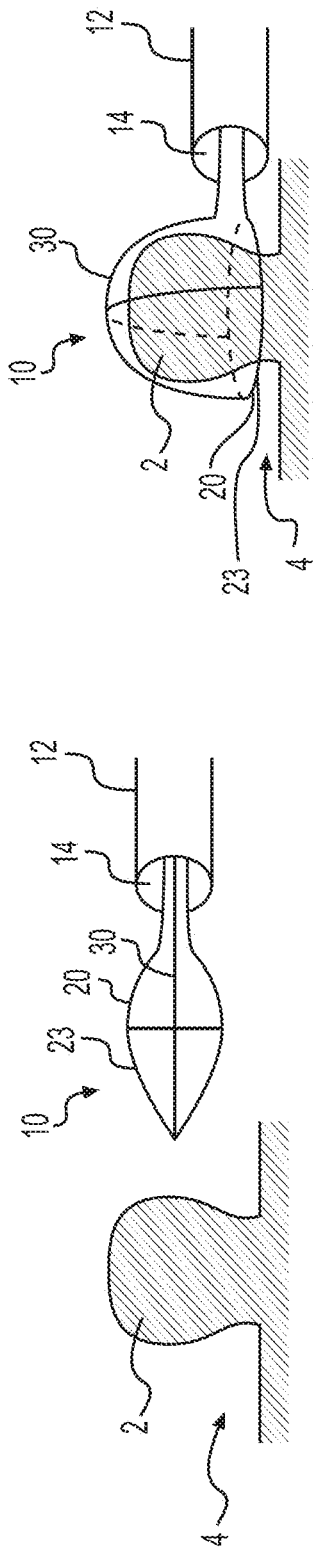
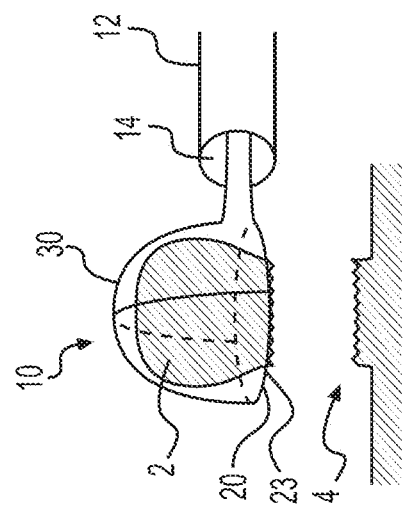
FIG. 3A
FIG. 3B
FIG. 3C

RETAINING POLYPECTOMY DEVICE

CROSS-REFERENCE TO RELATED APPLICATIONS

This application claims the benefit of priority to U.S. Provisional Application No. 62/376,492, filed Aug. 18, 2016, which is incorporated by reference herein in its entirety.

TECHNICAL FIELD

Aspects of the present disclosure generally relate to medical devices and procedures. In particular, aspects of the present disclosure relate to medical devices for, for example, manipulating, resecting, grasping, and/or collecting tissue, such as, for example, snare devices.

BACKGROUND

Medical devices, such as endoscopes or other suitable introduction devices, are employed for a variety of diagnostic and surgical procedures, such as endoscopy, laparoscopy, arthroscopy, gynoscopy, thoracoscopy, and cystoscopy, etc. Many of these procedures are carried out for purposes of tissue resection, which may include removal of tissue of an organ or a gland to treat tumors, infestations, and the like. In particular, such procedures may be carried out by inserting an insertion device into a patient's body through a surgical incision, or via a natural anatomical orifice (e.g., mouth, vagina, or rectum), and performing the procedure or operation.

Snare devices, in particular, have been used in many medical procedures, including Endoscopic Mucosal Resection (EMR) and Endoscopic Sub-mucosal Resection (ESR), polypectomy, mucosectomy, etc., for resecting tissue from a target site. A snare device may include a snare loop formed by snare wire(s), which engages the tissue intended to be resected. The snare loop is controlled and operated at a proximal end of the device through a suitable actuating mechanism. However, in many conventional snare devices, the tissue may eject or disconnect from the snare once severed. Not only should the tissue be recaptured, but the tissue may also disappear from the medical professional's field of view, further complicating recapture and resection.

The devices and methods of the current disclosure may rectify some of the deficiencies described above or address other aspects of the prior art.

SUMMARY

Examples of the present disclosure relate to, among other things, medical devices such as snares, and related methods of use thereof. Each of the examples disclosed herein may include one or more of the features described in connection with any of the other disclosed examples.

In one example, a medical device may comprise a snare loop; and an elastic member that connects at least two sides of the snare loop, wherein the elastic member is configured to transition from an unexpanded state where the elastic member is in a plane of the snare loop to an expanded state where the elastic member is outside the plane of the snare loop, the snare loop having a same shape when the elastic member is in the unexpanded shape and the expanded shape.

The medical device may further include one or more of the following features. According to this example, the elastic member may be linked to an elastic member handle, and the elastic member can transition from the unexpanded state to the expanded state through action of the elastic member handle. Furthermore, the elastic member can transition to the expanded state when the elastic member is pressed against tissue. The medical device may further includes a sheath, wherein the elastic member is in a contracted state when inside the sheath and transitions to an unexpanded state when outside the sheath. The snare loop may be linked to a snare handle at a proximal end of the medical device, and action of the snare handle may control the movement of the snare loop. The elastic member may connect a distal end of the snare loop to an elastic member handle located at a proximal end of the medical device. The snare loop and the elastic member may extend distally out of a lumen of an insertion device. The snare loop may include teeth or sharp edges. The snare loop may be conductive to provide a cautery current, and the elastic member may be nonconductive. The plane may be a single plane, and all of the elastic member, from a proximal end of the snare loop to a distal end of the snare loop, may be in the single plane in the unexpanded state. The snare loop may be connected to a snare handle by a single snare wire.

In some examples, the elastic member may have a cross-like configuration connecting edges of the snare loop and a distal end of the snare loop to an elastic member handle. The elastic member may have a V-shaped configuration, either pointing proximally or pointing distally, connecting edges of the snare loop and a distal end of the snare loop to an elastic member handle. The elastic member may include at least four elongate members connecting edges of the snare loop and a distal end of the snare loop to an elastic member handle, wherein the elongate members intersect interior to the snare loop. The snare loop may connect to a snare handle, the elastic member may connect to an elastic member handle that translates relative to the snare handle, and the device may further include a sheath connected to a sheath handle that translates relative to both of the snare handle and the elastic member handle.

In another example, a medical device may include a sheath having a lumen, the sheath connected to a sheath handle at a proximal end of the sheath; a snare extending through the lumen, including a snare loop at a distal end of the snare, and connected to a snare handle at a proximal end of the snare, the snare handle translating relative to the sheath handle; and an elastic member connected to the snare loop, spanning an area defined by the snare loop, and connected to an elastic member handle, wherein the elastic member handle translates relative to the snare handle and the sheath handle.

According to this example, the medical device may further include one or more of the following features. The elastic member can transition to an expanded state when the elastic member is pressed against tissue. The elastic member may be configured to transition from an unexpanded state to an expanded state, wherein when in the unexpanded state, all of the elastic member, from a proximal end of the snare loop to a distal end of the snare loop, is in a single plane of the snare loop. The at least one snare wire may be conductive to provide a cautery current, and the elastic member may be nonconductive. The elastic member may have a cross-like configuration connecting edges of the snare loop and a distal end of the snare loop to the elastic member handle. The elastic member may have a V-shaped configuration, either pointing proximally or pointing distally, connecting edges of the snare loop and a distal end of the snare loop to the elastic member handle.

Another example is a method of treatment to remove tissue with a snare loop and an elastic member connecting at least two sides of the snare loop, comprising: introducing the snare loop and the elastic member to a tissue site, with the snare loop and the elastic member being in a single plane; transitioning the elastic member from an unexpanded state in the single plane to an expanded state, in which the elastic member is out of the single plane; severing the tissue via the snare loop; and retaining the severed tissue via the snare loop and the elastic member.

According to this example, the elastic member may be transitioned from the unexpanded state to the expanded state by action of an elastic member handle, without affecting a shape of the snare loop. Severing the tissue may include at least partially closing the snare loop, moving the snare loop distally or proximally, or cauterizing the tissue with a cautery current applied by the snare loop. The method may further include slackening the elastic member and aspirating the removed tissue in a proximal direction. The elastic member may be slackened by action of an elastic member handle, without affecting a shape of the snare loop.

It may be understood that both the foregoing general description and the following detailed description are exemplary and explanatory only and are not restrictive of the disclosure, as claimed.

BRIEF DESCRIPTION OF THE DRAWINGS

The accompanying drawings, which are incorporated in and constitute a part of this specification, illustrate exemplary aspects of the present disclosure and together with the description, serve to explain the principles of the disclosure.

FIGS. 3A-3C illustrate the operation of the snare portion of FIG. 1.

DETAILED DESCRIPTION

Reference will now be made in detail to examples of the present disclosure described above and illustrated in the accompanying drawings. Wherever possible, the same reference numbers will be used throughout the drawings to refer to the same or like parts.

The terms "proximal" and "distal" are used herein to refer to the relative positions of the components of an exemplary medical device. When used herein, "proximal" refers to a position relatively closer to the exterior of the body or closer to a medical professional using the medical device. In contrast, "distal" refers to a position relatively further away from the medical professional using the medical device, or closer to the interior of the body. As used herein, the terms "comprises," "comprising," or like variation, are intended to cover a non-exclusive inclusion, such that a device or method that comprises a list of elements does not include only those elements, but may include other elements not expressly listed or inherent thereto. Unless stated otherwise, the term "exemplary" is used in the sense of "example" rather than "ideal."

The present disclosure is drawn to medical devices such as snare devices, and related methods of use thereof.

Figure 1:
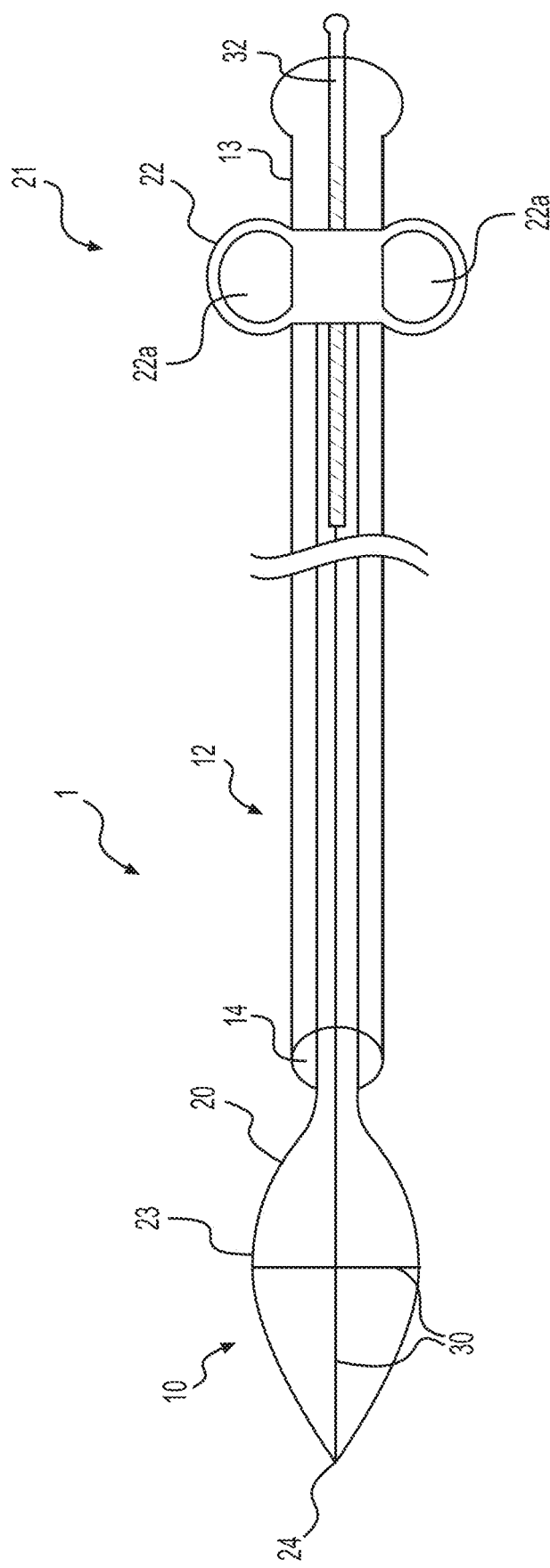
FIG. 1 illustrates an exemplary snare portion in an extended state.

FIG. 1 depicts a tissue removal device 1 with a snare portion 10 and a sheath 12. Snare portion 10 includes a snare wire 20, a snare handle 22, an elastic member 30, and an elastic member handle 32. The sheath 12 connects to a sheath handle 13 at a proximal end of the sheath 12. A device handle 21 at the proximal end of tissue removal device 1 includes sheath handle 13, snare handle 22, and elastic member handle 32, the interactions of which will be described further herein.

Snare portion 10 may be surrounded by sheath 12 and translate within a lumen 14 of sheath 12. Snare wire 20 may be a single, continuous monofilament or multifilament piece of material, such as a wire or coil, and may be formed in a loop at the distal end of the snare wire 20 to form a snare loop 23. Snare wire 20 alternatively may be formed of two pieces of material that are joined, for example by welding, soldering, or crimping, to form snare loop 23. Snare wire 20 may be formed of any appropriate material, such as, for example, Nitinol or stainless steel.

Snare loop 23 may form a circular enclosure through which it may surround and/or engage tissue. Snare loop 23 may also form an elliptical or oblong shape, or any shape that may surround and/or engage tissue. Snare loop 23 may be heat set into an arcuate, circular, or otherwise curved shape as shown in FIG. 1, and may include a tip 24 at the distal end. Tip 24 may be atraumatic.

Snare loop 23 may further include teeth or the like (not shown) configured for cutting, severing, and/or grasping tissue therewith. Snare loop 23, along with snare wire 20, may also be conductive to cauterize and cut tissue.

Snare wire 20 may extend proximally through and out of the proximal end of lumen 14 of sheath 12 to a proximal portion of tissue removal device 1, where snare wire 20 may be associated with any appropriate user interface such as, for example, snare handle 22. The proximal end of snare wire 20 may be coupled to snare handle 22 via a securement device such as, for example, a hypotube or crimp (not shown).

Snare handle 22 may slide relative to and on sheath handle 13 to control the movement of snare wire 20, and its snare loop 23, relative to sheath 12. Snare handle 22 may include a number of other structural features, including finger rings 22a and a plug (not shown) for connection to a source of cautery current. Snare wire 20 may be moved by snare handle 22 any suitable distance, at any suitable speed, and/or with any suitable amount of force.

Snare handle 22 may be configured to remain outside of a patient's body during a procedure and may allow a user to control snare loop 23, for example, by applying an axially directed pushing or pulling force on snare wire 20, to extend snare loop 23 out of the distal end of sheath 12 or retract snare loop 23 into the distal end of sheath 12, respectively. Extending snare loop 23 out of the distal end of sheath 12 may cause snare loop 23 to transition from a contracted state to an expanded state. Likewise, retracting snare loop 23 into the distal end of sheath 12 may cause snare loop 23 to transition back from an expanded state to a contracted state. Snare handle 22 may also be configured to control the snare loop 23 to engage, grasp, cut, sever, collect, and/or cauterize tissue.

As shown in FIG. 1, elastic member 30 may span from one edge of the snare loop 23 to another edge of snare loop 23, and may also connect the distal end of the snare loop 23, any other portion of snare loop 23, or the tip 24 to the proximal device components associated with device handle 21. For example, elastic member 30 may connect the edges of the snare loop 23 and connect tip 24 to elastic member handle 32 at the proximal end of device 1, through lumen 14.

Figure 2A:
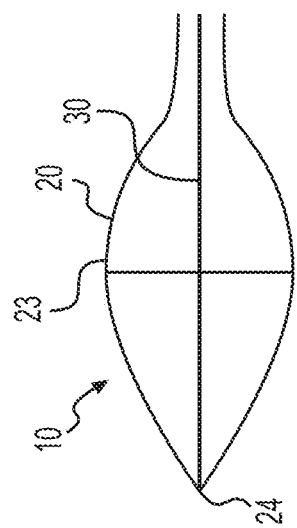
FIGS. 2A-2D each illustrates a top view of a distal portion of an exemplary snare portion with varied elastic member arrangements.
Figure 2B:
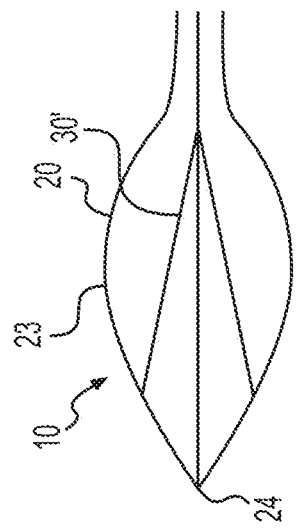

FIGS. 2A-2D illustrate top views of various arrangements that elastic member 30 may take relative to the snare loop 23. For example, elastic member 30 may have a cross-like configuration in its connection of the edges of the snare loop 23 and tip 24 to elastic member handle 32 (FIG. 2A). In that configuration, one portion of elastic member 30 extends longitudinally along a longitudinal axis of the device 1 to the tip 24, and another portion of elastic member 30 is transverse (and in one embodiment, perpendicular) to the first portion of elastic member 30.

Figure 2C:
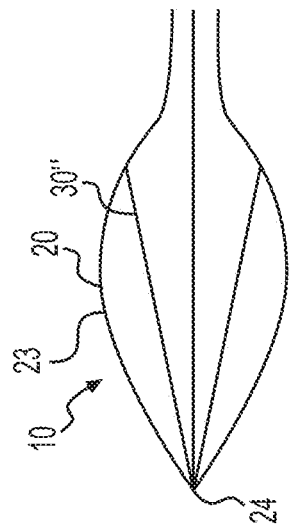

Elastic member 30', 30" may connect tip 24 to elastic member handle 32 and connect the edges of snare loop 23 in a V-shaped configuration, either pointing proximally (FIG. 2B) or pointing distally (FIG. 2C). In either V-shaped configuration, one portion of elastic member 30', 30" extends longitudinally along a longitudinal axis of the device 1 to the tip 24. When the V-shaped configuration points proximally (FIG. 2B), another portion of elastic member 30' extends from a distal portion (but proximal to tip 24) of one side of snare loop 23 to a more proximal portion of the first portion of elastic member 30' and then to a distal portion (but proximal to tip 24) of the other side of snare loop 23. When the V-shaped configuration points distally (FIG. 2C), another portion of elastic member 30" extends from a proximal portion of one side of snare loop 23 to a more distal portion of the first portion of elastic member 30" (and in one embodiment, to tip 24) and then to a proximal portion of the other side of snare loop 23.

Figure 2D:
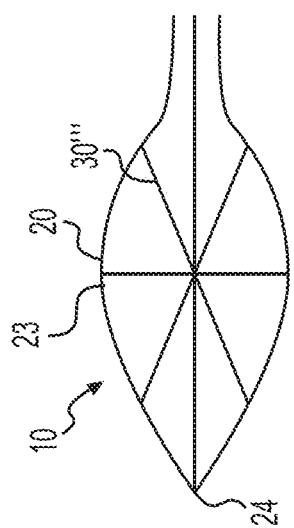

Elastic member 30''' may include at least four elongate members connecting tip 24 to elastic member handle 32 and connecting the edges of snare loop 23 both through a cross-like configuration and through angled members, where the elongate members intersect interior to the snare loop 23 (FIG. 2D). In this configuration, the first elongate member of elastic member 30''' may extend longitudinally along a longitudinal axis of device 1 to the tip 24. Another elongate member of elastic member 30''' may connect two sides of snare loop 23 and be transverse (and in one embodiment, perpendicular) to the first elongate member of elastic member 30'''. The other two elongate members of elastic member 30''' may each connect a distal portion of one side of snare loop 23 to a proximal portion of another side of snare loop 23. Alternatively, the other two elongate members of elastic member 30''' may extend in V-shaped configurations, either pointing distally or proximally as discussed above, and in one embodiment, the pivot of each V-shaped configuration is the intersection point of the first two elongate members.

In the aforementioned arrangements, elastic member 30 may comprise one integral elastic thread, may comprise two elastic threads, or may comprise more than two discrete elastic threads to form the particular arrangement. At or near each point of connection to the snare loop 23, elastic member 30 can bend or pivot relative to the snare loop 23, in any direction. Such connection can be made through any suitable connection method or structure, including glue or other adhesive, brazing, welding, soldering, heat-treating or the like.

Elastic member 30 may be made of any appropriate material, including polymers, polyurethane and its copolymers, ethylene vinyl-acetate, polyethylene terephthalate (PET), polyolefins, cellulosics, polyam ides, acrylonitrile butadiene styrene copolymers, Styrene Isoprene Butadiene (SIBS) Block Copolymers, acrylics, poly(glycolide-lactide) copolymer, Tecothane, PEBAX®, poly(γ-caprolactone), poly(γ-hydroxybutyrate), polydioxanone, poly(γ-ethyl glutamate), polyiminocarbonates, poly(ortho ester), and/or polyanhydrides. Blends of the above polymers may also be employed. Such materials may provide the elastic member 30 with different elasticities and rigidities. Materials of differing elasticities and rigidities may have different benefits depending on what type of tissue is being removed, the hardness of the tissue, the size of the tissue, etc. Additionally, the materials that form elastic member 30 may be heat resistant and/or nonconductive.

Elastic member 30 connects to elastic member handle 32, either directly by extending through lumen 14 to elastic member handle 32 or indirectly via an elongate member (like a wire or coil) extending through lumen 14 of sheath 12 and connecting elastic member 30 to elastic member handle 32. Elastic member handle 32 may be configured to remain outside of a patient's body during a procedure and may allow a user to control elastic member 30 through a movement of elastic member handle 32 relative to snare handle 22 and sheath handle 13. For example, elastic member 30 may be transitioned from an unexpanded state to an expanded state, or may be tightened or slackened, by pushing or pulling elastic member handle 32 or otherwise manipulating elastic member handle 32 relative to snare handle 22 and sheath handle 13 to impart an action to elastic member 30. In addition, because elastic member 30 is coupled to snare loop 23, action of snare handle 22 to translate snare loop 23 relative to sheath 12 may also tighten or slacken elastic member 30.

Sheath 12 with lumen 14 is rigidly attached to sheath handle 13 at the proximal end of tissue removal device 1. The rigid attachment may include, for example, welding, a locking configuration, use of an adhesive, or integrally forming sheath 12 with sheath handle 13. As discussed, snare handle 22 may slide on and over, and translate relative to, sheath handle 13. Elastic member handle 32 may translate or otherwise move relative to sheath handle 13 and snare handle 22. Elastic member handle 32 may be a rod that extends through a center of both sheath handle 13 and snare handle 22. Sheath handle 13 may include appropriately placed proximal and distal stops to limit the relative proximal and distal translation of snare handle 22 and elastic member handle 32.

Tissue removal device 1 will be described as a polyp removing and retaining device; however, it is understood that tissue removal device 1 may be used to remove any type of tissue from a target site inside a patient. For example, tissue removal device 1 may be alternatively used to remove obstructions in the gastrointestinal tract, biliary tract, urinary tract, ear canal and nasal passages: including but not limited to, bile duct stones and gallstones, stones in the kidneys or ureter, benign prostatic hyperplasia (BPH), tumors, blood clots, fibrous tissue, abscesses and cysts, feces in a rectal impaction, adenoids, hypertrophied turbinates and foreign bodies.

An insertion device (not shown) may deliver medical instruments, such as tissue removal device 1, into a subject's body. The insertion device may be inserted into a variety of body openings, lumens, and/or cavities. For example, the insertion device may be inserted into any portion of a urinary tract, such as a ureter, a gastrointestinal lumen, such as an esophagus or colon, a vascular lumen, and/or an airway. According to aspects of the present disclosure, the insertion device may be a ureteroscope, an endoscope, a hysteroscope, a bronchoscope, a cystoscope, or a similar device. Alternatively, the insertion device may be a catheter or other sheath. The insertion device may be single-use and disposable, or multiple-use and non-disposable. The insertion device may have a circular cross-sectional shape and include at least one inner lumen in which the medical instrument inserts. The insertion device also may include other functionalities, such as imaging, light, aspiration, and irrigation.

FIGS. 3A-3C illustrate the procedure by which snare loop 23 and elastic member 30 of tissue removal device 1 may capture and retain a polyp 2. In the illustrated procedure, tissue removal device 1 may be delivered to a polyp removal site 4 via any insertion device. Tissue removal device 1 may have an insertion configuration, where snare loop 23 and elastic member 30 are retracted proximally into lumen 14 of sheath 12 by positioning snare handle 22 in its most proximal position. In such an insertion configuration, snare loop 23 and elastic member 30 may be in a contracted state.

As shown in FIG. 3A, upon introduction to the polyp removal site 4, distal movement of snare handle 22, relative to sheath handle 13, causes snare loop 23 and elastic member 30 to extend distally from sheath 12 and transition from the insertion configuration to an extended state. It is noted that snare portion 10 may take any configuration shown in FIGS. 2A-2D in the procedure depicted in FIGS. 3A-3C. In the initial extended state, snare loop 23 and elastic member 30 may be in a single plane of the snare loop 23, with elastic member 30 in an unexpanded state. Then, snare loop 23 may encounter polyp 2, and extend over polyp 2, reaching its neck. This may cause elastic member 30 to transition from the unexpanded state to an expanded state by the force imparted by polyp 2, such that both snare loop 23 and elastic member 30 surround polyp 2 (FIG. 3B). As mentioned, the action of the elastic member handle 32 (movement proximally relative to snare handle 22 and sheath handle 13) may transition elastic member 30 from the unexpanded state to the expanded state without any force imparted by polyp 2 (or in combination with force imparted by polyp 2), such that snare loop 23 and elastic member 30 may surround polyp 2. Such action of the elastic member handle 32 may also control the tightness or slackness of elastic member 30 before or after elastic member 30 has contacted polyp 2 to surround polyp 2.

Snare loop 23 may sever polyp 2 from polyp removal site 4 through tightening, which may be imparted via snare handle 22 (movement of snare handle 22 proximally relative to sheath handle 13 and elastic member handle 32). Tightening snare loop 23 may also tighten the hold of elastic member 30 about polyp 2, preventing ejection of polyp 2 by way of elastic member 30 being connected to the edges of snare loop 23. Snare loop 23 may use other techniques to sever polyp 2, including providing a proximal or distal force to polyp 2 and/or transmitting a cautery current through a conductive snare wire 20 to snare loop 23 as snare loop 23 is closed about polyp 2 such that the polyp 2 is excised. Snare loop 23 may also sever polyp 2 through other tissue removal techniques, such as teeth or sharp edges on a radially inward surface of snare loop 23. These severing actions by snare loop 23 may be implemented via action of snare handle 22.

As polyp 2 is severed by snare loop 23, elastic member 30 serves to surround and retain polyp 2 to inhibit escape of polyp 2 from the snare portion 10. Then, action on snare handle 22 (proximal movement relative to sheath handle 13) may cause snare loop 23 to return proximally toward sheath 12 and/or the insertion device with polyp 2 retained in order to remove polyp 2 from polyp removal site 4. Snare loop 23 may be retracted proximally away from the polyp removal site 4 and out of the patient, either together with the insertion device or alone through the insertion device.

Alternatively or additionally, a vacuum (not shown) may be positioned in the insertion device or extend distally out of the insertion device at the distal end of the insertion device to aid in resection of polyp 2 and its removal from the patient. For example, after polyp 2 has been resected (FIG. 3C), snare loop 23 may be positioned proximate the vacuum and action on snare handle 22 and/or elastic member handle 32 may loosen or slacken the hold of snare loop 23 and elastic member 30 on polyp 2 such that polyp 2 may be aspirated proximally out of snare loop 23 and elastic member 30 and away from polyp removal site 4 through the vacuum. Then, the procedure may be repeated to sever and remove another polyp or multiple polyps, allowing for an efficient and reliable polyp removal procedure.

While principles of the present disclosure are described herein with reference to illustrative aspects for particular applications, it should be understood that the disclosure is not limited thereto. Those having ordinary skill in the art and access to the teachings provided herein will recognize additional modifications, applications, aspects, and substitution of equivalents all fall within the scope of the aspects described herein. Accordingly, the disclosure is not to be considered as limited by the foregoing description.

We claim:

1. A medical device, comprising:
   a snare loop; and
   an elastic member that connects at least two sides of the snare loop, wherein the elastic member is configured to transition from an unexpanded state where the elastic member is in a plane of the snare loop to an expanded state where the elastic member is outside the plane of the snare loop, the snare loop having a same shape when the elastic member is in the unexpanded shape and the expanded shape, wherein the elastic member can transition to the expanded state by pressing the elastic member against tissue,
   wherein the elastic member has a V-shaped configuration, either pointing proximally or pointing distally, connecting edges of the snare loop and a distal end of the snare loop to an elastic member handle.

2. The medical device of claim 1, wherein the elastic member is linked to an elastic member handle, and wherein the elastic member can transition to the expanded state by pressing the elastic member against tissue without action of the elastic member handle.

3. The medical device of claim 1, wherein the elastic member is linked to an elastic member handle, and the elastic member can transition from the unexpanded state to the expanded state through action of the elastic member handle.

4. The medical device of claim 1, further comprising a sheath, wherein the elastic member is in a contracted state when inside the sheath and transitions to an unexpanded state when outside the sheath.

5. The medical device of claim 1, wherein the snare loop is linked to a snare handle at a proximal end of the medical device, and wherein action of the snare handle controls the movement of the snare loop.

6. The medical device of claim 1, wherein the elastic member connects a distal end of the snare loop to an elastic member handle located at the proximal end of the medical device.

7. The medical device of claim 1, wherein the plane is a single plane, and all of the elastic member, from a proximal end of the snare loop to a distal end of the snare loop, is in the single plane in the unexpanded state.

8. The medical device of claim 1, wherein the snare loop connects to a snare handle, the elastic member connects to an elastic member handle that translates relative to the snare handle, and the device further includes a sheath connected to a sheath handle that translates relative to both of the snare handle and the elastic member handle.

9. The medical device of claim 1, wherein the snare loop is conductive to provide a cautery current; and wherein the elastic member is nonconductive.

10. The medical device of claim 1, wherein the elastic member has the V-shaped configuration pointing distally, wherein one portion of the elastic member extends longitudinally along a longitudinal axis of the medical device to a tip of the snare loop, and wherein another portion of elastic member extends from a proximal portion of one side of snare loop to a more distal portion of the first portion of the elastic member and then to a proximal portion of the other side of the snare loop.

11. The medical device of claim 1, wherein the elastic member is formed of a heat resistant material, wherein the snare loop is formed of nitinol or stainless steel, and wherein the tip of the snare loop is atraumatic.

12. A medical device, comprising:
a sheath having a lumen, the sheath connected to a sheath handle at a proximal end of the sheath;
a snare extending through the lumen, including a snare loop at a distal end of the snare, and connected to a snare handle at a proximal end of the snare, the snare handle translating relative to the sheath handle; and
an elastic member connected to the snare loop, spanning an area defined by the snare loop, and connected to an elastic member handle, wherein the elastic member handle translates relative to the snare handle and the sheath handle,
wherein the elastic member has a V-shaped configuration, either pointing proximally or pointing distally, connecting edges of the snare loop and a distal end of the snare loop to the elastic member handle.

13. The medical device of claim 12, wherein the elastic member can transition to an expanded state when the elastic member is pressed against tissue.

14. The medical device of claim 12, wherein the elastic member is configured to transition from an unexpanded state to an expanded state, wherein when in the unexpanded state, all of the elastic member, from a proximal end of the snare loop to a distal end of the snare loop, is in a single plane of the snare loop.

15. The medical device of claim 12, wherein the at least one snare wire is conductive to provide a cautery current, and wherein the elastic member is nonconductive.

16. The medical device of claim 12, wherein the elastic member has the V-shaped configuration pointing distally, wherein one portion of the elastic member extends longitudinally along a longitudinal axis of the medical device to a tip of the snare loop, and wherein another portion of elastic member extends from a proximal portion of one side of snare loop to a more distal portion of the first portion of the elastic member and then to a proximal portion of the other side of the snare loop.

17. The medical device of claim 12, wherein the elastic member is linked to an elastic member handle, and wherein the elastic member can transition to the expanded state by pressing the elastic member against tissue without action of the elastic member handle.

18. The medical device of claim 12, wherein the elastic member is linked to an elastic member handle, and the elastic member can transition from the unexpanded state to the expanded state through action of the elastic member handle.

19. The medical device of claim 18, further comprising a snare handle, and wherein the elastic member handle is movable relative to the snare handle to transition the elastic member from the unexpanded state to the expanded state.

20. The medical device of claim 12, wherein the elastic member is formed of a heat resistant material, and wherein the snare loop is formed of nitinol or stainless steel.

* * * * *